United States Patent
Ollila et al.

(10) Patent No.: US 11,869,680 B2
(45) Date of Patent: Jan. 9, 2024

(54) TREATING A TREATMENT VOLUME WITH THERAPEUTIC RADIATION USING A MULTI-LEAF COLLIMATION SYSTEM

(71) Applicant: Varian Medical Systems International AG, Steinhausen (CH)

(72) Inventors: Santtu T.T. Ollila, Helsinki (FI); Janne I. Nord, Espoo (FI); Jarkko Y. Peltola, Tuusula (FI)

(73) Assignee: Varian Medical Systems International AG, Steinhausen (CH)

(*) Notice: Subject to any disclaimer, the term of this patent is extended or adjusted under 35 U.S.C. 154(b) by 97 days.

(21) Appl. No.: 15/941,326

(22) Filed: Mar. 30, 2018

(65) Prior Publication Data
US 2019/0304617 A1 Oct. 3, 2019

(51) Int. Cl.
*G21K 1/04* (2006.01)
*A61N 5/10* (2006.01)

(52) U.S. Cl.
CPC ............ *G21K 1/046* (2013.01); *A61N 5/1031* (2013.01); *A61N 5/1036* (2013.01); *A61N 5/1045* (2013.01)

(58) Field of Classification Search
CPC ......... G21K 1/02–046; G21K 5/00–10; A61N 5/103–1039; A61N 5/1042–1047;
(Continued)

(56) References Cited

U.S. PATENT DOCUMENTS 7,283,611 B1 10/2007 Luan
2005/0058245 A1* 3/2005 Ein-Gal ............... A61N 5/1042
378/65
(Continued)

FOREIGN PATENT DOCUMENTS

CN 101636199 A 1/2010
JP 2001276240 A 10/2001
(Continued)

OTHER PUBLICATIONS

Younge KC et al. Penalization of aperture complexity in inversely planned volumetric modulated arc therapy. Medical Physics 39(11), p. 7160-7170, Nov. 2012 (Year: 2012).*
(Continued)

*Primary Examiner* — Christine H Matthews
*Assistant Examiner* — Joshua Daryl D Lannu
(74) *Attorney, Agent, or Firm* — Fitch, Even, Tabin & Flannery LLP (57) ABSTRACT

A control circuit optimizes a radiation treatment plan for a patient treatment volume using an automatically iterating optimization process that optimizes as a function, at least in part, of predetermined cost functions, wherein at least one of the cost functions favors apertures for the multi-leaf collimation system having local curvature that deviates only minimally from a reference curvature. By one approach the control circuit determines the reference curvature as a function, at least in part, of at least one of setting the reference curvature to a static minimal local curvature, a shape of a projective mapping of the treatment volume onto an isocenter plane, and/or a fluence map associated with an amount of radiation to be administered to the treatment volume from a particular direction. By one approach the control circuit dynamically determines when to employ one or more such cost functions.

11 Claims, 6 Drawing Sheets

(58) Field of Classification Search
CPC ...... A61N 5/1077; A61N 5/1081–1082; A61N 2005/1032–1041; A61N 5/1031; A61N 5/1036; A61N 5/1045; H05H 2007/007; H05H 7/001; H05H 9/00–048; H05H 2277/10–11

See application file for complete search history.

(56) References Cited

U.S. PATENT DOCUMENTS

| | | |
|---|---|---|
| 2005/0123098 A1 | 6/2005 | Wang |
| 2006/0256915 A1 | 11/2006 | Otto |
| 2008/0298550 A1 | 12/2008 | Otto |
| 2010/0046706 A1* | 2/2010 | Moreau ................. A61N 5/103 378/65 |
| 2001/0091015 | 4/2011 | Yu |
| 2018/0020535 A1* | 1/2018 | Cooley ................. A61N 5/103 |
| 2018/0028113 A1 | 2/2018 | Otto |

FOREIGN PATENT DOCUMENTS

| | | | |
|---|---|---|---|
| WO | 2005018742 A1 | 3/2005 | |
| WO | WO-2008039991 A1 * | 4/2008 | ........... A61N 5/1047 |
| WO | 2013167733 A1 | 11/2013 | |

OTHER PUBLICATIONS

Calvert, James. "Degree of Curvature". Last revised Jun. 20, 2004. http://mysite.du.edu/~jcalvert/railway/degcurv.htm Wayback machine capture dated Mar. 1, 2016. (Year: 2004).*

Younge, Kelly C. et al.; Penalization of aperture complexity in inversely planned volumetric modulated arc therapy, Medical Physics, vol. 39, No. 11; Nov. 2012; pp. 7160-7170.

Locke, Christopher Barry et al., "Trajectory Optimization in Radiotherapy Using Sectioning (TORUS)"; Department of Radiation Oncology, Stanford University School of Medicine, Stanford, CA; Apr. 4, 2017; 42 pages.

PCT Search Report and Written Opinion from International Patent Application No. PCT/EP2019/057133, dated Jun. 28, 2019; 13 pages.

Chinese First Office Action from related Chinese Patent Application No. 201980023230.0 dated Aug. 22, 2022, English translation included; 24 pages.

* cited by examiner

TREATING A TREATMENT VOLUME WITH THERAPEUTIC RADIATION USING A MULTI-LEAF COLLIMATION SYSTEM

TECHNICAL FIELD

These teachings relate generally to treating a patient's treatment volume with therapeutic radiation and more particularly to the use of a multi-leaf collimator.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient while using a particular radiation treatment platform. For example, many treatment plans provide for exposing the target volume to possibly varying dosages of radiation from a number of different directions. Arc therapy, for example, comprises one such approach.

Such treatment plans are often optimized prior to use. It will be understood that the expression "optimize," "optimized," and "optimizing" as used herein should not be confused with the idea of identifying an objectively "optimum" plan that is superior to all other possible plans. Instead, such optimization comprises iteratively assessing alternatives to a given plan to typically identify a series of successively-better plans. This can comprise, for example, trying and evaluating iterative alterations to each (or many) of the aforementioned operating parameters.

As a more specific example in these regards, when optimizing a radiation treatment plan with respect to a multi-leaf collimator, the optimization process typically seeks an optimal position for each pair of leaves independent of all other leaf pairs (for each field of exposure). This independent consideration inherently relies upon a decoupledness of different pairs of leaves that often results in jagged aperture shapes for the collimator. In such a case, every other leaf protrudes from a common front as defined by an average over the positions of leaves that are involved with modulating radiation for a given part of a treatment target. While such a plan can appear to offer excellent target coverage and excellent performance with respect to sparing any organs-at-risk, such complex aperture shapes can themselves give rise to problems.

For example, clinical quality assurance issues can arise due to discrepancies between the predicted dose distribution and the actual measured result. Such problems can be particularly noticeable when treating small treatment volumes using small apertures (where leaf tip separation may be no more than a fraction of a millimeter). In such a case the estimated efficacy of a plan may underestimate the maximum dose level by, for example, 7 percent as compared to film measurements. Complex aperture shapes can also contribute to undue and premature wear and tear on the motors that move the leaves in a multi-leaf collimator that occurs as a result of largely redundant to-and-fro leaf movement.

BRIEF DESCRIPTION OF THE DRAWINGS

The above needs are at least partially met through provision of the treating a treatment volume with therapeutic radiation using a multi-leaf collimation system described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

SUMMARY

Generally speaking, these various embodiments pertain to an apparatus that facilitates treating a patient's treatment volume with therapeutic radiation using a multi-leaf collimation system. The apparatus includes a control circuit configured to optimize a radiation treatment plan for the patient treatment volume using an automatically iterating optimization process that optimizes as a function, at least in part, of predetermined cost functions, wherein at least one of the cost functions favors apertures for the multi-leaf collimation system having local curvature that deviates only minimally from a reference curvature. The apparatus also includes a radiation treatment platform operably configured to administer the therapeutic radiation to the patient in accordance with the radiation treatment plan as optimized by the control circuit.

By one approach the control circuit determines the aforementioned reference curvature as a function, at least in part, of at least one of setting the reference curvature to a static minimal local curvature, a shape of a projective mapping of the treatment volume onto an isocenter plane, and/or a fluence map associated with an amount of radiation to be administered to the treatment volume from a particular direction.

By one approach the control circuit determines when to employ one or more such cost functions. This can comprise, for example, switching use of only one such cost function on and off. This can also comprise, if desired, switching between two or more different cost functions in these regards. The control circuit can be configured to make such determinations as a function, for example, of the patient's anatomy and/or a remaining fluence to be administered per the radiation treatment plan.

These teachings are highly flexible in practice. In lieu of the foregoing or in combination therewith, for example, the control circuit can be configured to optimize as a function of a cost function that favors larger apertures for the multi-leaf collimation system.

By one approach these teachings will accommodate introducing a new planning component that penalizes jagged edges of multi-leaf collimator apertures in a cost function of the optimization process. This can comprise, for example, configuring the component to favor apertures of minimal local curvature. In such a case the corresponding cost is accrued only when adjacent leaf pairs modulate the same spatially continuous part of a given treatment target.

By one approach, these teachings will accommodate determining where and when the aforementioned constraint is applied at each iteration of the optimization process. Accordingly, new candidate solutions that tend to favor large apertures typically result.

So configured, these teachings produce radiation treatment plans that more consistently produce clinical results that reasonably accord with predicted results and without loss in clinical plan quality. Depending upon the particular implementation, these teachings can lead to a decrease in the number of collimator apertures and/or an increase in the mean size of collimator apertures. These teachings can also often reduce the jaggedness of aperture edges and/or reduce the number of monitor units (MUs) in the treatment plan.

DETAILED DESCRIPTION

Figure 1:
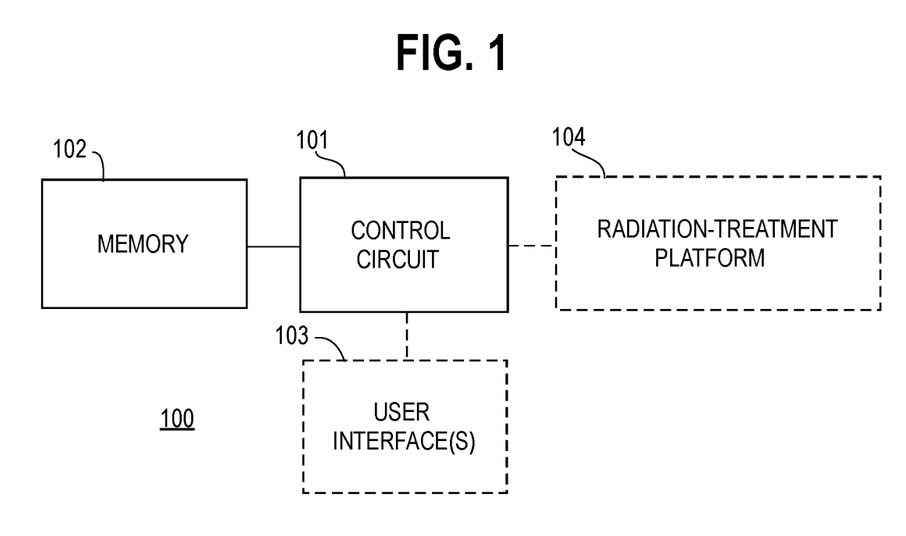
FIG. 1 comprises a block diagram as configured in accordance with various embodiments of these teachings.

These and other benefits may become clearer upon making a thorough review and study of the following detailed description. The teachings described herein are readily enabled using any of a wide variety of available and/or readily configured platforms, including partially or wholly programmable platforms as are known in the art or dedicated purpose platforms as may be desired for some applications. Referring now to the drawings, and in particular to FIG. 1, an illustrative approach to such an apparatus 100 will now be provided.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

In this example the control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information regarding predetermined cost functions, patient anatomy, and the like as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

By one optional approach the control circuit 101 operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

The control circuit 101 can also optionally operably couple (directly or indirectly) to a radiation treatment platform 104 configured to deliver therapeutic radiation to a corresponding patient in accordance with an optimized radiation treatment plan as described herein.

In a typical application setting the radiation treatment platform 104 will include an x-ray source (for example, a radio-frequency (RF) linear particle accelerator-based (linac-based) x-ray source, such as the Varian Linatron M9). A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) and high energy electrons.

A typical radiation treatment platform 104 may also include one or more support surfaces (such as a couch) to support the patient during the treatment session, a gantry or other mechanism to permit selective movement of the x-ray source (along, for example, an arcuate pathway), and one or more components (such as jaws, multi-leaf collimators (including both mono-layer multi-leaf collimators and multi-layer multi-leaf collimators), and so forth) to provide selective beam shaping and/or beam modulation as desired.

As the foregoing elements and systems are well understood in the art, further elaboration in these regards is not provided here except where otherwise relevant to the description.

Figure 2:
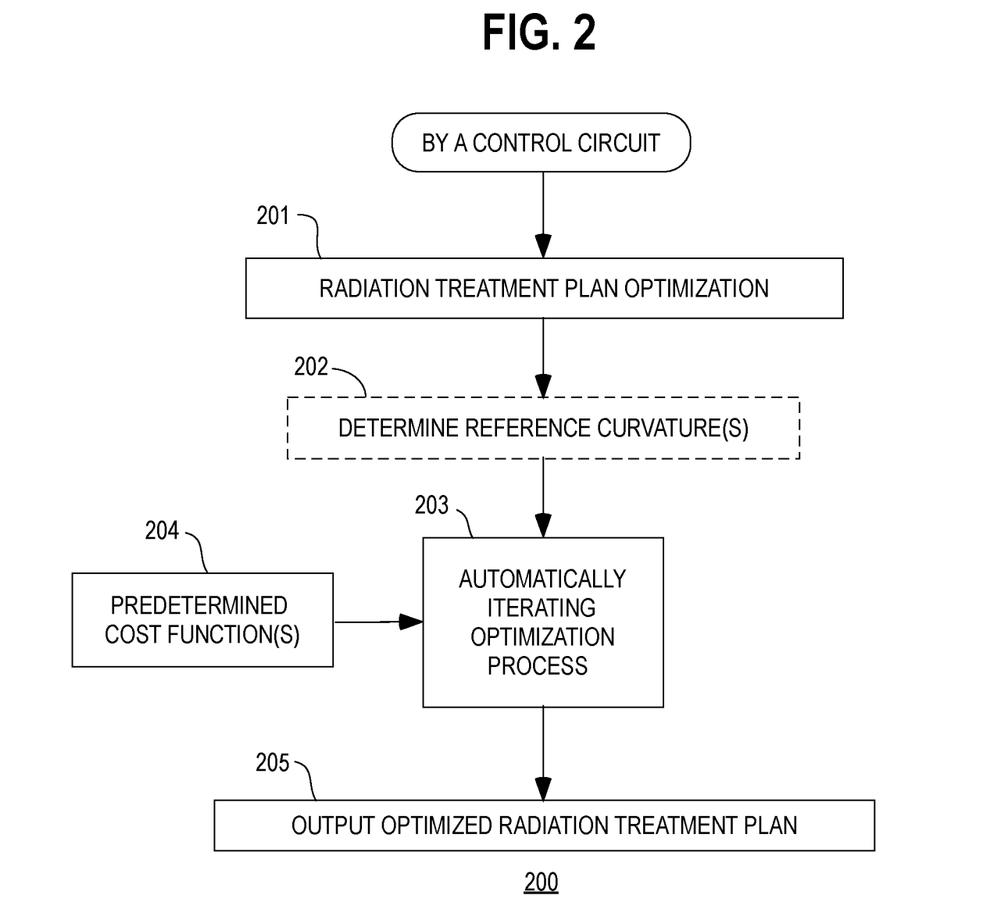
FIG. 2 comprises a flow diagram as configured in accordance with various embodiments of these teachings.

FIG. 2 presents a process 200 that can be carried out by the aforementioned control circuit 101. At block 201, the process 200 begins a radiation treatment plan optimization process of choice. At optional block 202, the process 200 provides for determining one or more reference curvatures. These teachings will accommodate using a reference curvature of 0 degrees if desired. Other curvatures can be accommodated as well including but not limited to curvatures that represent a part of a circle, a part of an ellipse, or a part of any other arc of choice. This process 200 will accommodate a variety of ways of determining the reference curvature including calculating the reference curvature using one or more corresponding equations or selecting one or more reference curvatures from a plurality of candidate reference curvatures.

By one approach, and as suggested above, the control circuit 101 determines the reference curvature as a function, at least in part, of setting the reference curvature to a static minimal local curvature (such as 0 degrees, 0.01 degrees, 0.5 degrees, or the like). Viewed as a plane curve, the curvature of the reference curvature at a given point is a measure of how sensitive its tangent line is to moving the point to other nearby points. Given any curve C and a point P on it, there is a unique circle or line that most closely approximates that curve near P (this circle is often referred to as the osculating circle). The curvature of C at P may then be defined as the curvature of that circle or line. Accordingly, the curvature can be defined as the reciprocal of the radius of that osculating circle.

By another approach, if desired, the control circuit 101 determines the reference curvature as a function, at least in part, of a shape of a projective mapping of the treatment volume onto an isocenter plane. (The "isocenter" will be understood to refer to the point in space relative to the radiation treatment platform 104 about which various components of the machine rotate.) And by yet another approach, in lieu of the foregoing or in combination therewith, the control circuit 101 can be configured to determine the reference curvature as a function, at least in part, of a fluence map associated with an amount of radiation to be administered to the treatment volume from a particular direction. ("Fluence" will be understood to represent radiative flux integrated over time; those skilled in the art will recognize that fluence comprises a fundamental metric in dosimetry (i.e., the measurement and calculation of an absorbed dose of ionizing radiation in matter and tissue).)

At block 203 this process supports an automatically iterating optimization process of choice. This optimization occurs as a function of one or more predetermined cost functions 204 in accordance with well understood prior art technique. Contrary to the prior art, however, in this process 200 at least one of these predetermined cost functions 204 favors apertures for a multi-leaf collimation system having local curvature that deviates only minimally from the aforementioned reference curvature. The dimensions that make the curvature "local" can vary with the needs of the application setting but will typically be measured or defined here as corresponding to the width of three adjacent leaves of the multi-leaf collimator.

Generally speaking, an optimization process using such a cost function will favor apertures having local curvature that deviate only minimally from the aforementioned reference curvature by increasing the cost associated with increasing deviations from the standard set by the reference curvature. The maximum extent to which the cost increases and/or the rate by which the cost increases for increasing deviations can vary as desired with the application setting.

In many application settings it will be unlikely that a solution featuring zero deviation from the standard set by the reference curvature can be achieved. That is neither surprising nor unacceptable. The goal, instead, is to seek solutions that minimize such deviations to the extent they nevertheless occur. By one approach the user can be given a selectable choice (e.g. on an integer scale from 1 to 5, or from low to very high) regarding how much to weigh or prefer aperture simplicity. The optimal choice can depend on the application. As one illustrative example, prostate/intracranial cases (where the target tends to have a roundish shape) are likely to be compatible with a high preference for simple apertures. By contrast, and as another example, head and neck treatments typically require a significant amount of modulation due to the complex shape of the projection of the treatment target(s). To accommodate such disparate possibilities, the user can be given the ability to specify an upper bound on the cost associated with the aperture shape.

Figure 3:
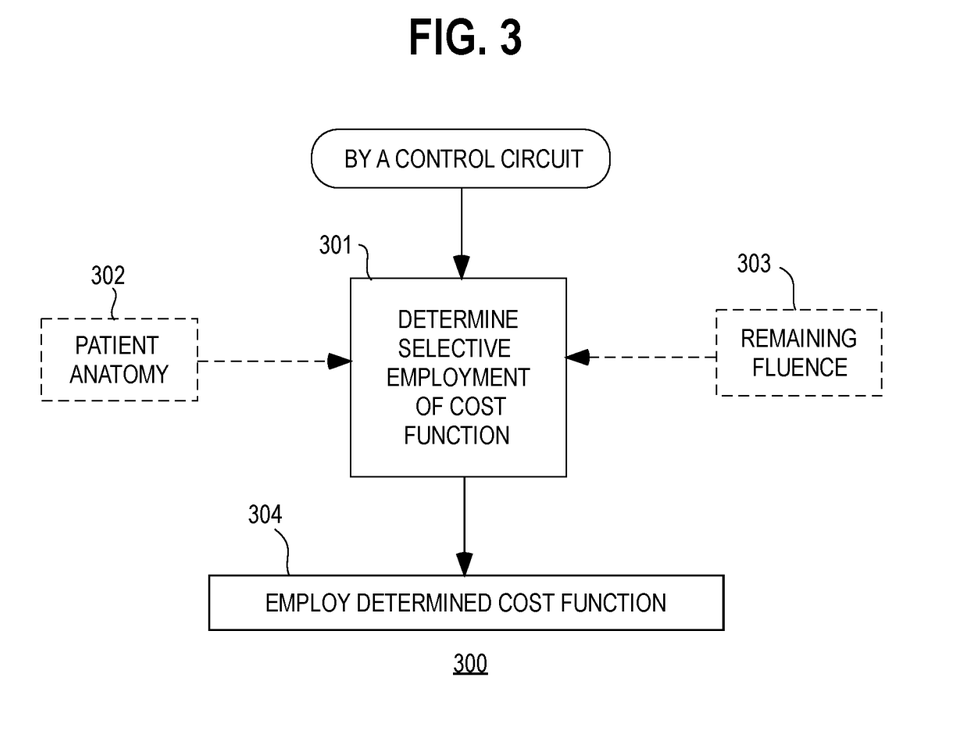
FIG. 3 comprises a flow diagram as configured in accordance with various embodiments of these teachings.

If desired, the automatic iterative optimization process 203 can include determinations regarding selective employment of the aforementioned cost function that favor apertures for the multi-leaf collimation system having local curvature that deviates only minimally from a reference curvature. FIG. 3 presents an illustrative example in these regards.

At block 301 the control circuit 101 can determine (on an iteration-by-iteration and/or leaf-by-leaf basis) whether to selectively employ the aforementioned cost function. So configured, this cost function can be employed when and as appropriate but not employed in other cases. (Further description in these regards appears further herein.) This determination can be made as a function of, for example, anatomy for the patient 302 (such as, for example, a shape of the patient's treatment volume and/or the shape of one or more organs-at-risk) and/or remaining fluence 303 to be administered per the radiation treatment plan.

In lieu of the foregoing or in combination therewith, this determination regarding selective employment of a cost function can comprise selecting when to switch amongst a plurality of different reference curvatures. For example, a first cost function based upon a first reference curvature may be appropriate for use at one part of the patient's anatomy and a second cost function based upon a second, different reference curvature may be appropriate for use at a different part of the patient's anatomy.

Upon determining to utilize such a cost function at a particular time, place, or iteration, at block 304 the control circuit 101 employs the determined cost function.

These teachings are highly flexible in practice and will accommodate further modifications and/or supplemental features. As one example in these regards, and referring again to FIG. 2, the aforementioned predetermined cost functions 204 can optionally include a cost function that favors larger apertures for the multi-leaf collimation system.

By one approach the control circuit 101 can be configured to determine when to selectively employ such a cost function, including whether to selectively employ such a cost function for each pair of leaves for a given multi-leaf collimator.

Accordingly, by one approach the control circuit 101, at each iteration of the optimization process, calibrates the relative magnitude of this aperture shape sensitivity with respect to other optimization objectives. During the sampling phase of the process, where positioning of the multi-leaf collimator leaves is considered, the control circuit 101 can generate a candidate solution by favoring large apertures and then construct trial patterns for those adjacent leaves that fulfill the modulation requirement. The control circuit 101 can then optimize the positions of the leaves in the presence of the new component (favoring, for example, minimal local curvature) for groups of adjacent leaves that fulfill the modulation requirement. Changes to the total cost function due to the foregoing are evaluated and the changes incorporated into the developing plan if those changes in fact reduce the value of the cost function of the plan.

At the conclusion of the optimization process, at block 205 the control circuit 101 outputs an optimized radiation treatment plan. The above-described radiation-treatment platform 104 can then be operably configured to administer therapeutic radiation to the patient in accordance with this optimized radiation treatment plan.

Figure 4:
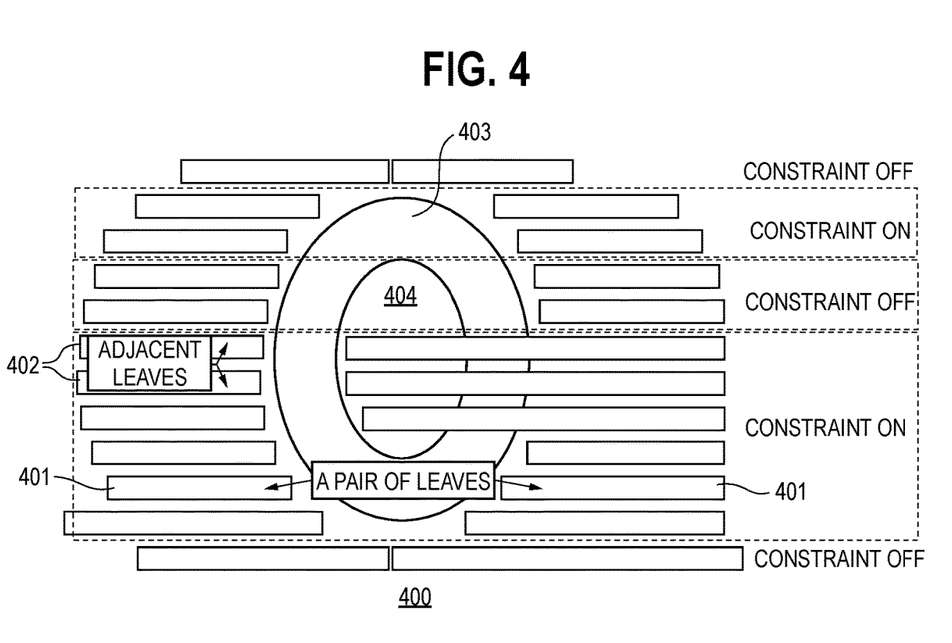
FIG. 4 comprises a schematic representation as configured in accordance with various embodiments of these teachings.

FIG. 4 presents an illustrative example in the foregoing regards. This example includes a multi-leaf collimator 400 having a plurality of leaf pairs. Reference numeral 401 depicts a first pair of leaves as an illustrative example. Each leaf also has at least one adjacent leaf. The expression "adjacent" will be understood to not refer to the other leaf that is paired to such a leaf. In a multi-layer multi-leaf collimator, a given leaf may have several "adjacent" leaves: one on either side in the same layer as well as one or several above or below depending on the relative spatial offsets as viewed on the isocenter plane. For most relevant purposes, one set of layers of leaves is attached to a carriage on one side (such as the left side) and the other set of layers of leaves is attached to a carriage on the opposite side (such as the right side). Adjacency therefore can pertain to leaves a) on the same carriage and b) being next to one another in the same layer or having overlap in projection if on a different layer. Reference numeral 402 depicts two leaves that are adjacent one another. Reference numeral 403 refers to the patient's treatment volume.

In this example the aforementioned cost function favors apertures featuring minimal local curvature. The corresponding cost is accrued as a function of the magnitude of local curvature between adjacent leaves in the case where leaf pairs are associated with adjacent leaves that modulate the same spatially continuous projection of the treatment target 403.

This example also illustrates switching between use and nonuse of the constraint imposed by the aforementioned cost function. In this example the decision to employ or not employ the constraint depends, at least in part, upon the shape of the patient treatment volume 403. This patient treatment volume 403 is generally ring-shaped. As a result, the nontargeted interior 404 constitutes tissue to be protected from radiation. As illustrated, employing or not employing this particular constraint during optimization has a significant effect upon the positioning of the right-side leaves with respect to that interior portion 404.

As a further illustrative example, the coupling between adjacent leaves i and i+1 can be chosen as $$C_{i,i+1} = \lambda f(|x_i - x_{i+1}|)$$

where the function can comprise, for example, a polynomial.

Figure 5:
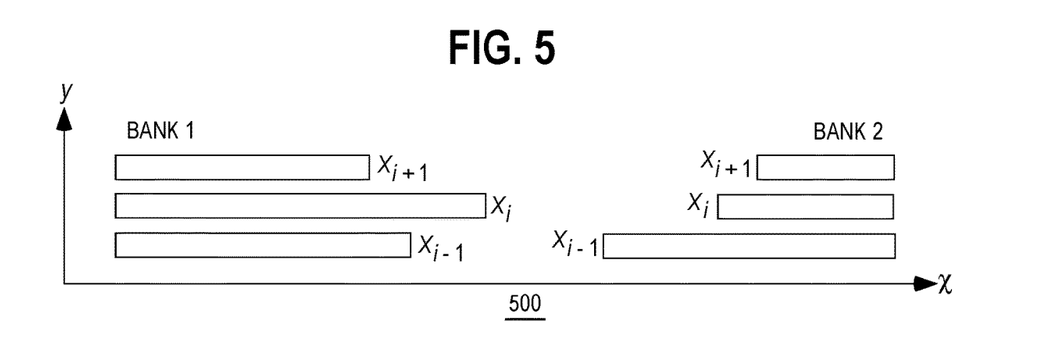
FIG. 5 comprises a schematic representation as configured in accordance with various embodiments of these teachings.
Figure 6:
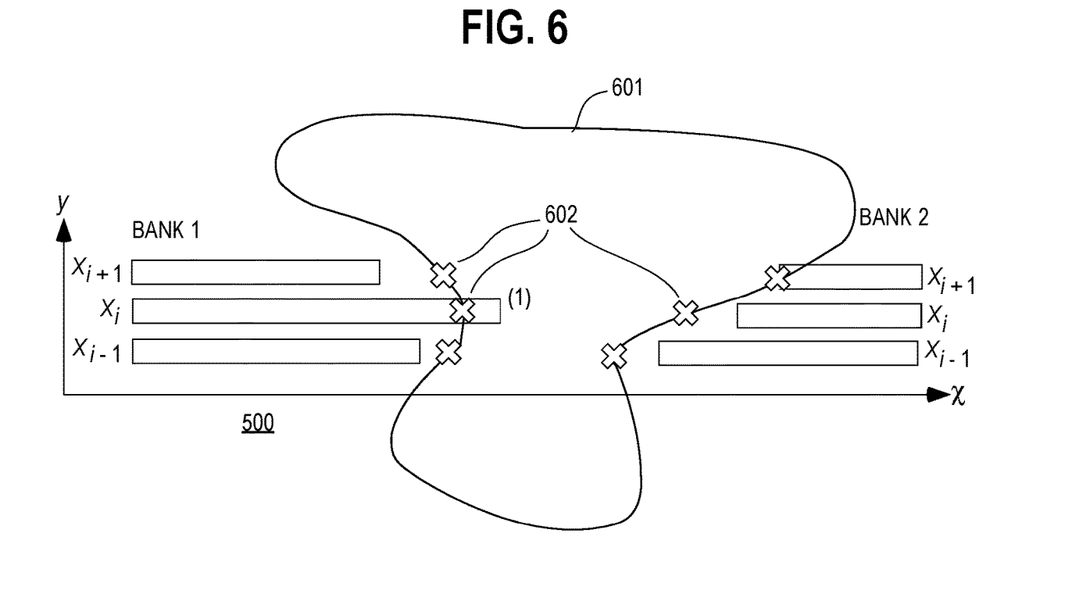
FIG. 6 comprises a schematic representation as configured in accordance with various embodiments of these teachings.

By way of illustration and without intending any particular limitations by way of specificity, FIGS. 5 and 6 present a simple example where only three pairs of multi-leaf collimator leaves 500 are shown for the sake of simplicity and clarity. Bank 1 includes the left-side leaves of each pair while Bank 2 includes the right-side leaves of each such pair. The centrally-disposed leaves have leaf tips that are denoted as $X_i$. Accordingly, the leaves disposed above those centrally-disposed leaves have tips that are denoted as $X_{i+1}$ while the leaves disposed below those centrally-disposed leaves have tips that are denoted as $X_{i-1}$.

Local curvature k can be defined as $$k = \frac{d^2X/dy^2}{\left(1+\left(\frac{dX}{dy}\right)^2\right)^{\frac{3}{2}}}$$

where y denotes position in a direction perpendicular to leaf motion.

FIG. 6 presents the multi-leaf collimator leaves 500 shown in FIG. 5 in context with a reference shape 601. "X" marks (some being denoted by reference numeral 602) serve to identify mapped positions on the reference shape 601 that each correlate (uniquely) to one of the leaves. In this simple example there are a total of six discrete leaf tips and six mapped positions on the reference shape that yield a total of 12 (x,y) coordinates. Using these 12 coordinates, one can calculate the actual local curvatures defined by the leaf tips as $$k_i^{(j)} = k(x_i^{(j)}; x_{i-1}^{(j)}, x_{i+1}^{(j)}, w_i, w_{i-1}, w_{i+1})$$

$$k_i^{(ref,j)} = k(x_i^{(ref,j)}; x_{i-1}^{(ref,j)}, x_{i+1}^{(ref,j)}, w_i, w_{i-1}, w_{i+1})$$

at Banks j=1,2 for leaf pair i using finite-difference approximations to spatial derivatives in k. $w_i$ specifies the width of the leaves of leaf pair i. At the end points, one-sided derivatives and/or other approximations can be employed.

With continued reference to the nomenclature expressed above, by one approach this process can employ terms proportional to $$\propto |k_i^j - s(\{x\},\{x^{ref}\},MLC)k_i^{ref,j}|$$

where the switching function s decides whether the process strives for a local reference curvature of zero or that defined by some reference shape.

In the above-provided examples the multi-leaf collimator comprises a single-layer collimator. These teachings can be employed with a multi-layer multi-leaf collimator if desired. In that case, these same teachings can also take into account a local coupling between the layers.

Figure 7:
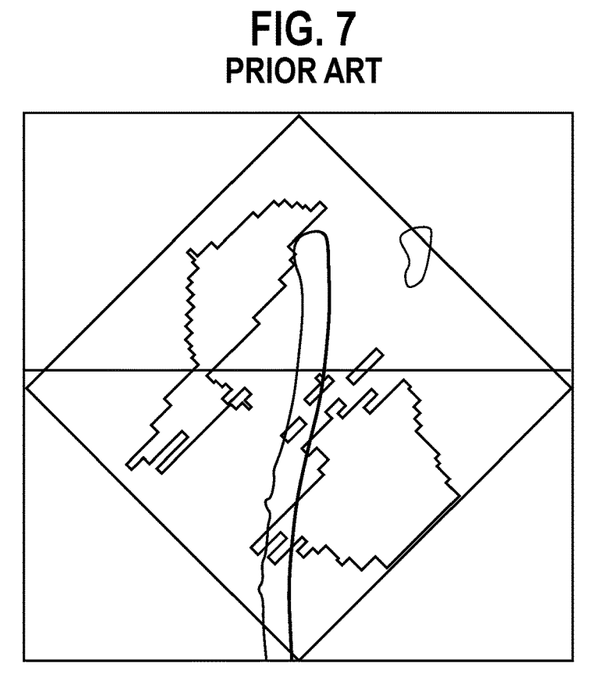
FIG. 7 comprises a screenshot that illustrates a prior art approach.
Figure 8:
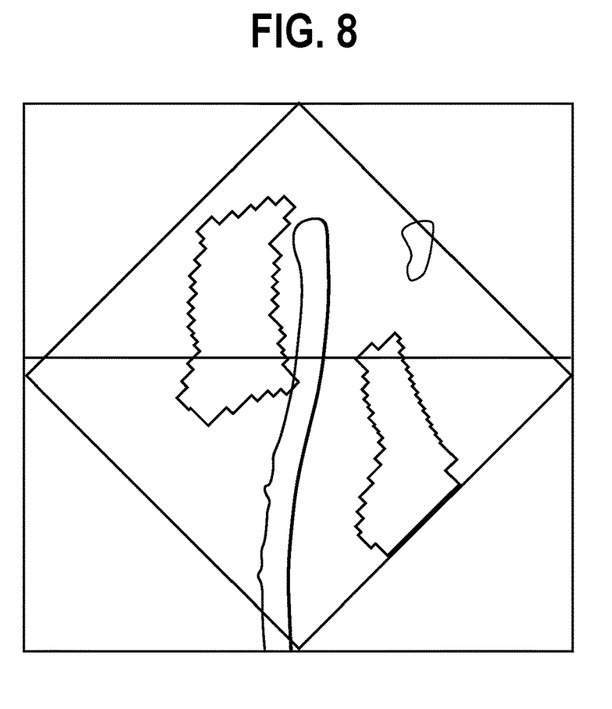
FIG. 8 comprises a screenshot that illustrates an approach in accordance with various embodiments of these teachings.

So configured, these teachings help avoid at least many of the problems described above while helping to ensure the utility and efficacy of a resultant radiation treatment plan. FIG. 7 presents an illustrative example of prior art aperture settings where the optimization process lacked a cost function as described herein. The resultant apertures include both a considerable number of very small apertures as well as larger apertures having complicated, jagged shapes. FIG. 8 presents the same patient presentation but where the aperture settings reflect use of the cost function described herein.

Here, there are fewer small apertures and the larger apertures are more regular in shape and feature reduced jaggedness. Put another way, these teachings decreased the number of apertures and increased the mean size of those apertures as compared to a similar or identical prior art approach that only differed for lack of a cost function that favors apertures having local curvature that deviates only minimally from a reference curvature.

It will be further appreciated that these teachings are especially useful in application settings that employ volumetric modulated arc radiotherapy (VMAT) techniques, where only one or where multiple axis (such as any one or more of the gantry, couch, or collimator) move while the radiation is administered.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus to facilitate treating a patient's treatment volume with therapeutic radiation using a multi-leaf collimation system, the apparatus comprising:
    a control circuit configured to:
        determine a reference curvature as a function, at least in part, of relative differences of a plurality of laterally adjacent leaf positions, and relative differences of a plurality of laterally adjacent leaf-widths of the multi-leaf collimation system; and
        optimize a radiation treatment plan for the patient's treatment volume using an automatically iterating optimization process that optimizes as a function, at least in part, of predetermined cost functions, wherein at least one of the cost functions favors apertures for the multi-leaf collimation system having local curvature that deviates only minimally from the reference curvature by increasing a cost associated with increasing deviations of the local curvature with respect to the reference curvature; and
    a radiation treatment platform operably configured to administer the therapeutic radiation to the patient in accordance with the radiation treatment plan as optimized by the control circuit.

2. The apparatus of claim 1 wherein the control circuit is further configured to determine the reference curvature as a function, at least in part, of at least one of:
    a shape of a projective mapping of the treatment volume onto an isocenter plane; and
    a fluence map associated with an amount of radiation to be administered to the treatment volume from a particular direction.

3. The apparatus of claim 1 wherein the control circuit is further configured to determine when to selectively employ the at least one of the cost functions that favors apertures for the multi-leaf collimation system having local curvature that deviates only minimally from the reference curvature.

4. The apparatus of claim 3 wherein the control circuit is further configured to determine when to selectively employ the at least one of the cost functions that favors apertures for the multi-leaf collimation system having local curvature that deviates only minimally from the reference curvature as a function, at least in part, of at least one of:
    anatomy for the patient; and
    remaining fluence to be administered per the radiation treatment plan.

5. The apparatus of claim 3 wherein the control circuit is further configured to determine when to selectively employ the at least one of the cost functions that favors apertures for the multi-leaf collimation system having local curvature that deviates only minimally from the reference curvature by selecting when to switch amongst a plurality of different reference curvatures.

6. The apparatus of claim 1 wherein at least another of the cost functions favors larger apertures for the multi-leaf collimation system.

7. The apparatus of claim 6 wherein the control circuit is further configured to determine when to selectively employ the at least one of the cost functions that favors larger apertures for the multi-leaf collimation system.

8. The apparatus of claim 7 wherein the control circuit is configured to determine whether to selectively employ the at least one of the cost functions that favors larger apertures for the multi-leaf collimation system for [each] one or more pairs of laterally adjacent leaves in the multi-leaf collimation system.

9. The apparatus of claim 1 wherein the multi-leaf collimation system comprises a multi-layer multi-leaf collimator.

10. An apparatus to facilitate treating a patient's treatment volume with therapeutic radiation using a multi-leaf collimation system, the apparatus comprising:
    a control circuit configured to:
        determine a reference curvature as a function, at least in part, of relative differences of a plurality of laterally adjacent leaf positions, and relative differences of a plurality of laterally adjacent leaf-widths of the multi-leaf collimation system; and
        optimize a radiation treatment plan for the patient's treatment volume using an automatically iterating optimization process that optimizes as a function, at least in part, of predetermined cost functions, wherein at least a first one of the cost functions favors apertures for the multi-leaf collimation system having local curvature that deviates only minimally from the reference curvature, by increasing a cost associated with increasing deviations of the local curvature with respect to the reference curvature, and a second one of the cost functions favors larger apertures for the multi-leaf collimation system; and
    a radiation treatment platform operably configured to administer the therapeutic radiation to the patient in accordance with the radiation treatment plan as optimized by the control circuit.

11. The apparatus of claim 10 wherein the control circuit is further configured to determine when to selectively employ the first one of the cost functions and the second one of the cost functions.

* * * * *